(12) United States Patent
Goldblatt

(10) Patent No.: US 7,514,393 B2
(45) Date of Patent: Apr. 7, 2009

(54) PREPARATION OF FUNCTIONAL MONOMERS FOR GRAFTING TO LOW MOLECULAR WEIGHT POLYALKENES AND THEIR USE IN THE PREPARATION OF DISPERSANTS AND LUBRICATING OIL COMPOSITIONS CONTAINING DISPERSANT POLYALKENES

(75) Inventor: Irwin L. Goldblatt, Edison, NJ (US)

(73) Assignee: Castrol Limited, Swindon (GB)

( * ) Notice: Subject to any disclaimer, the term of this patent is extended or adjusted under 35 U.S.C. 154(b) by 636 days.

(21) Appl. No.: 10/983,377

(22) Filed: Nov. 8, 2004

(65) Prior Publication Data

US 2005/0209113 A1   Sep. 22, 2005

Related U.S. Application Data

(60) Provisional application No. 60/523,959, filed on Nov. 21, 2003.

(51) Int. Cl.
   *C10L 1/22* (2006.01)
(52) U.S. Cl. .................................... 508/454
(58) Field of Classification Search ............ 508/466, 508/467, 454
   See application file for complete search history.

(56) References Cited

U.S. PATENT DOCUMENTS

| | | | |
|---|---|---|---|
| 3,873,459 A | 3/1975 | Pawlak et al. ............ 252/51.5 A |
| 4,092,255 A | 5/1978 | Chapelet et al. ............... 252/50 |
| 4,137,185 A | 1/1979 | Gardiner et al. |
| 4,146,489 A | 3/1979 | Stambaugh et al. ............ 252/50 |
| 4,160,739 A | 7/1979 | Stambaugh et al. |
| 4,320,019 A | 3/1982 | Hayashi ...................... 252/51.5 |
| 4,517,104 A | 5/1985 | Bloch et al. |
| 4,632,769 A | 12/1986 | Gutierrez et al. |
| 4,640,788 A | 2/1987 | Kapuscinski et al. ....... 252/51.5 |
| 4,693,838 A | 9/1987 | Varma et al. |
| 4,969,912 A * | 11/1990 | Kelman et al. ............... 128/898 |
| 5,167,845 A | 12/1992 | DeRosa et al. ............. 252/47.5 |
| 5,219,480 A | 6/1993 | Gutierrez et al. ........... 252/51.5 |
| 5,294,354 A | 3/1994 | Papke et al. |
| 5,298,565 A | 3/1994 | Lange et al. ................ 525/279 |
| 5,328,624 A | 7/1994 | Chung |
| 5,346,635 A | 9/1994 | Khorramian et al. |
| 5,424,357 A | 6/1995 | Larson ...................... 524/765 |
| 5,424,367 A | 6/1995 | Auda et al. .................. 525/285 |
| 5,427,702 A | 6/1995 | Chung et al. ............... 252/51.5 |
| 5,439,605 A | 8/1995 | Khorramian et al. |
| 5,523,008 A | 6/1996 | Boden et al. .................... 252/50 |
| 5,527,624 A * | 6/1996 | Higgins et al. .............. 428/523 |
| 5,663,126 A | 9/1997 | Boden et al. ................. 508/221 |
| 5,814,586 A | 9/1998 | Boden et al. ................. 508/221 |
| 5,874,389 A | 2/1999 | Boden et al. ................. 508/221 |
| 6,034,038 A | 3/2000 | Lockwood et al. |
| 6,100,224 A * | 8/2000 | Peiffer et al. ................ 508/235 |
| 6,300,289 B1 | 10/2001 | Boden et al. ................. 508/221 |
| 6,410,652 B1 | 6/2002 | Goldblatt et al. ............ 525/279 |
| 6,686,321 B2 | 2/2004 | Boden et al. |
| 6,939,420 B2 * | 9/2005 | Pollack .......................... 149/2 |
| 7,371,713 B2 | 5/2008 | Goldblatt et al. |
| 2006/0205611 A1 | 9/2006 | Sauer |

FOREIGN PATENT DOCUMENTS

| | | | |
|---|---|---|---|
| CN | 1137283 | 12/1996 | |
| DE | 196 07 641 A1 | 9/1997 | |
| EP | 0 000648 | 2/1979 | |
| EP | 0 336716 | 10/1989 | |
| EP | 0 352 070 | 1/1990 | |
| EP | 0 352 072 | 1/1990 | |
| EP | 0 438 848 | 7/1991 | |
| EP | 0837122 A2 | 4/1998 | |
| EP | 0 980 891 | 2/2000 | |
| EP | 1533293 | 5/2005 | |
| GB | 1 390 851 | 4/1975 | |
| GB | 1 531 945 | 11/1978 | |
| GB | 2 097 800 | 11/1982 | |
| IN | 738/MMNP/2004 | 4/2005 | |
| SG | 112056 | 6/2005 | |
| WO | WO 95/16744 | 6/1995 | |
| WO | WO 95/18199 | 7/1995 | |
| WO | WO 97/47709 | 12/1997 | |
| WO | WO 00/37449 | 6/2000 | |
| WO | WO 0119882 A1 | 3/2001 | ............. 225/6 |
| WO | WO 03/099890 | 12/2003 | |
| WO | WO2006-099250 | 9/2006 | |
| WO | WO2006116663 | 11/2006 | |

OTHER PUBLICATIONS

*Aldrich Handbook of Fine Chemicals*; 1996-1997; pp. 986; Catalogue No. 14 607-2 "N,N' Methylenebisacrylamide".
European Search Report corresponding to European Patent Application Serial No. 03734186.4-1214 dated Aug. 7, 2008, 5 pages.

* cited by examiner

*Primary Examiner*—Walter D. Griffin
*Assistant Examiner*—Frank C Campanell
(74) *Attorney, Agent, or Firm*—McAndrews, Held & Malloy, Ltd.

(57) ABSTRACT

A polyalkene dispersant comprised of low MW polyalkene having an average molecular weight range of about 300 to about 10,000 and an ethylenically-unsaturated, aliphatic or aromatic, nitrogen- and oxygen-containing graftable monomer and methods of making the same are disclosed. The monomers are formed by reacting an acylating agent with amines having one or more primary or secondary amine to form a reaction product. Graft polyalkene dispersants comprising such monomers are formed by grafting the reaction product to the polyalkene backbone. Also described is lubricating oil comprising base oil and the dispersant polyalkene as described above.

5 Claims, No Drawings

PREPARATION OF FUNCTIONAL MONOMERS FOR GRAFTING TO LOW MOLECULAR WEIGHT POLYALKENES AND THEIR USE IN THE PREPARATION OF DISPERSANTS AND LUBRICATING OIL COMPOSITIONS CONTAINING DISPERSANT POLYALKENES

This application claims the benefit of Provisional Patent Application No. 60/523,959, filed on Nov. 21, 2003.

OBJECTS OF THE INVENTION

The present invention relates to novel functional monomers and dispersant polyalkenes comprising such monomers.

The present invention further relates to low MW polyalkene backbones which have been grafted with ethylenically unsaturated, aliphatic or aromatic mono-, bi- and multi-functional monomer mixtures containing oxygen and nitrogen atoms.

The present invention further relates to methods for manufacturing these novel monomers and the dispersant graft polyalkenes comprising such monomers.

The present invention further relates to lubricating oil compositions containing the dispersant graft polyalkenes in amounts effective to function as dispersants and potentially as low MW viscosity index improvers.

It is also contemplated that the molar proportions of the grafted mono, bi and multi-functional monomer to low MW polyalkene ratio may be 0.2:1, 0.5:1, 1:1, 2:1, 4:1 and as much as 8:1 of grafted monomer: moles polyalkene backbone.

SUMMARY OF THE INVENTION

The present invention provides novel monomers and methods of making such monomers. Such monomers may be used to prepare dispersants or dispersant viscosity index improvers (DVII's). One aspect of the invention is the preparation of a reaction product comprising one or more ethylenically unsaturated, aliphatic or aromatic monomers having nitrogen and oxygen atoms. For example, the reaction product obtained by reacting maleic anhydride and triethylene tetramine. The reaction product is a mixture that contains, among other components, the mono-maleimide and corresponding amic acid of triethylene tetramine as well as the di-maleimide and corresponding di-amic acid of triethylene tetramine. The graftable compounds of the reaction product are then grafted onto the low MW polyalkene using free radical initiators.

The term "reaction product" as used in this specification refers to one or more compounds formed by the reaction of one, two or more reactants. Thus, it may include more than one chemical compound formed from the combination of the acylating agent and the amine, and in such instances, the term "reaction product" will be understood to refer to all such chemical compounds. The term "monomer" as used in this specification refers to the graftable, ethylenically unsaturated, aliphatic or aromatic nitrogen- and oxygen-containing compound(s) of the reaction product. The monomers may be mono-, bi- or multi-functional. The graftable monomer(s) may, but need not, be recovered from the product mixture before carrying out the grafting reaction. The present method may also comprise the step of recovering one or more graftable compounds from the reaction product of the acylating agent and the amine.

Another aspect of the invention is the graft reaction product of a low MW polyalkene with an ethylenically unsaturated, aliphatic or aromatic mono-, bi- or multi-functional monomer having from 3 to about 50 carbon atoms in addition to nitrogen and oxygen atoms. The graft reaction product has a molar proportion of grafted monomer to polyalkene ratio of at least about 0.2:1, alternatively at least about 0.5:1, alternatively at least about 1:1, alternatively at least about 2:1, about 4:1, and as much as about 8:1.

Another aspect of the invention is a method of making a dispersant or low MW viscosity index improver. According to this invention, a graftable monomer and a low MW polyalkene are provided. In some embodiments the low MW polyalkene has pendant unsaturated sites for grafting. Sufficient initiator is provided to graft the graftable monomer to the polyalkene. In some embodiments, grafting of the monomer onto the polyalkene backbone is carried out after reacting the low MW polyalkene with chlorine. In some embodiments, grafting of the monomer mixture onto the polyalkene backbone is carried using the "ene" reaction.

Another aspect of this invention is the grafting of an ethylenically-unsaturated, aliphatic or aromatic, hydrocarbon monomer containing both nitrogen and oxygen atoms onto a low MW polyalkene to form a dispersant moiety. To meet the objectives of the invention, it is preferable to react the polyalkene so that it contains at least about 0.2 mole of monomer per mole of polyalkene, or alternatively, 0.5 mole of monomer per mole of polyalkene or, alternatively, 1 mole of monomer per mole of polyalkene or, alternatively, 2 moles of monomer per mole of polyalkene or, alternatively, 4 moles of monomer per mole of polyalkene or, alternatively, as much as 8 moles of monomer per mole of polyalkene, though the ratio is not critical for all aspects of the invention. The low MW polyalkene of the present invention (hereinafter alternatively referred to as the polyalkene or the low MW polyalkene) has a number average molecular weight of from about 300 to about 10000, preferably from about 500 to about 8000, or preferably from about 900 to about 5000 or more preferably from about 900 to about 4000. Particularly useful polyalkenes have number average molecular weights from about 1100 to about 3000.

In carrying out the reaction, the polyalkene may be reacted as a neat material or dissolved in a solvent forming a solution. The graftable monomer and an initiator are added to the polyalkene. The graftable monomer and/or the initiator can be added gradually to the polyalkene or they can be added together or introduced successively or introduced as aliquots of reactants. The rate of addition of the graftable monomer can be from 0.1% to 100% of the entire charge of monomer per minute. The rate of addition of the initiator can be from about 0.1% to about 100% of the initiator charge per minute. The reaction temperature is maintained at a level which gives rise to a satisfactory reaction initiation rate. In one embodiment, the graftable monomer and the initiator are each added at a uniform, relatively slow rate during the reaction.

The resulting graft polyalkene may have a monomer to polyalkene ratio of at least about 0.2:1, alternatively at least about 0.5:1, alternatively at least about 0.8:1, alternatively at least about 1:1, alternatively at least about 2:1, about 4:1, about 8:1, or even higher ratios.

In principle, the graft product from the polyalkene may be made by melt-blending and reacting a mixture consisting essentially of the graftable monomer mixture; a low MW polyalkene; and an initiator. The reaction is carried out at a temperature and under conditions effective to graft the monomer mixture onto the polyalkene. The graft reaction product under such circumstances exhibits a monomer to polymer ratio of at least about 0.2:1, alternatively at least about, 0.5:1 alternatively at least about 0.8:1, alternatively at least about 1:1, alternatively at least about 2:1, about 4:1, and as much as about 8:1, or possibly higher ratios.

Another aspect of the invention is lubricating oil comprising a hydrocarbon base oil and a grafted polyalkene as described above. The grafted polyalkene functions as a dispersant or as a dispersant with viscosity enhancing properties. The dispersant may be used in an amount which is from about 0.05% to 20% by weight solids of a lubricating oil composition.

DETAILED DESCRIPTION OF THE INVENTION

While the invention will be described in connection with one or more preferred embodiments, it will be understood that the invention is not limited to those embodiments. The invention includes all alternatives, modifications, and equivalents as may be included within the spirit and scope of the claims concluding this specification.

The novel bi- or multi-functional monomers according to the present invention are obtained by reacting acylating agents, such as maleic anhydride, with amines having more than one primary or secondary amine, such as triethylene tetramine. Mono-functional monomers are obtained, for example, by reacting maleic anhydride with amines having only one primary or secondary amine such as 4-aminodiphenylamine. For a more complete description of amines used to prepare mono-functional monomers see U.S. patent application Ser. No. 10/444,548 which is incorporated herein by reference.

The novel graft polyalkene (also referred to herein as dispersant polyalkene) according to the present invention is made by reacting a low MW polyalkene with a polar, ethylenically unsaturated, preferably nitrogen- and oxygen-containing, preferably heterocyclic and aromatic graftable monomer, in the presence of an initiator. The reaction may be carried out with either neat polyalkene, polyalkene dissolved in solvent, or neat polyalkene in melt form using an extrusion reactor.

In the following paragraphs are examples of reactants used in the preparation of (a) the bifunctional and higher graftable monomer mixtures, (b) grafted polyalkenes to form dispersants, and (c) lubricating oil compositions. Also, in the following examples are descriptions of the polyalkenes, acylating agents, amines, initiators, and solvents contemplated for use herein to make the bifunctional and higher graftable monomer mixtures and dispersants from polyalkenes.

I. Materials and Methods for Preparation of Bi-Functional and Higher Graftable Monomer Mixtures A. Solvents for Use in the Preparation of Bi-Functional and Higher Graftable Monomer Mixtures Useful solvents include volatile solvents which are readily removable from the monomer after the reaction is complete or ones which are not readily volatilized and removed after completion of the reaction. Any solvent may be used which can disperse or dissolve the reaction product and may be handled in such a way as not to participate appreciably in the reaction or cause side reactions to a material degree or interfere with subsequent processes which utilize the graftable monomer mixture. Several examples of solvents of this type include straight chain or branched chain aliphatic or alicyclic hydrocarbons, such as n-pentane, n-heptane, i-heptane, n-octane, i-octane, nonane, decane, cyclohexane, dihydronaphthalene, decahydronaphthalene, and relatively volatile aromatics such as toluene, xylene, and ethylbenzene and others not listed. Nonreactive halogenated aromatic hydrocarbons such as chlorobenzene, dichlorobenzene, trichlorobenzene, dichlorotoluene and others are also useful as solvents. Aliphatic or aromatic ketones, ethers, esters, formamides, carbonates, water etc., are also contemplated as solvents herein. Also contemplated are mixtures of solvents.

Examples of the ketones, ethers, esters, formamides, carbonates, etc. which are contemplated include, but are not limited to, acetone, methylethyl ketone, diethyl ketone, N,N-dimethylformamide, N,N-diethylformamide, N,N-dimethylacetamide, N-methyl pyrrolidone, diethyl carbonate, propylene carbonate, diethyl ether, dimethyl ether, isopropyl ether, 2-methoxyethyl ether, dioxane, dimethyl sulfoxide, butyl acetate, ethyl acetate, and dimethyl malonate.

The solvents useful here also include base oils or base stocks, as defined in ASTM D 6074-99, "Standard Guide for Characterizing Hydrocarbon Lubricant Base Oils" which may be suitable for incorporation into a final lubricating oil product. Any base oil may be used which can disperse or dissolve the reaction product without materially participating in the reaction or causing side reactions to an unacceptable degree. For example, solvent dewaxed and hydrocracked base oils, paraffin and isoparaffin fluids, base oils which contain low or moderate levels of aromatic constituents, and fluid poly-$\alpha$-olefins are contemplated for use herein. The use of base oils having aromatic constituents, while being less than optimum in some instances, is contemplated under this disclosure.

B. Acylating Agents for Use in the Preparation of Bi-Functional and Higher Graftable Monomer Mixtures In this specification, the terms olefinic unsaturation and ethylenic unsaturation are used interchangeably. The acylating agent has at least one point of olefinic unsaturation (in other words, C=C) in its structure. Usually, the point of olefinic unsaturation will correspond to —HC=CH— or —HC=CH$_2$. Acylating agents where the point of olefinic unsaturation is $\alpha$, $\beta$ to a carboxy functional group are very useful. Olefinically unsaturated mono-, di-, and polycarboxylic acids, the lower alkyl esters thereof, the halides thereof, and the anhydrides thereof represent typical acylating agents in accordance with the present invention. Preferably, the olefinically unsaturated acylating agent is a mono- or dibasic acid, or a derivative thereof such as anhydrides, lower alkyl esters, halides and mixtures of two or more such derivatives. "Lower alkyl" means alkyl groups of one to seven carbon atoms.

The acylating agent may include at least one member selected from the group consisting of monounsaturated $C_4$ to $C_{50}$, alternatively $C_4$ to $C_{20}$, alternatively $C_4$ to $C_{10}$, dicarboxylic acids monounsaturated $C_3$ to $C_{50}$, alternatively $C_3$ to $C_{20}$, alternatively $C_3$ to $C_{10}$, monocarboxylic acids and anhydrides thereof (that is, anhydrides of those carboxylic acids or of those monocarboxylic acids), and combinations of any of the foregoing (that is, two or more of those acids and/or anhydrides).

Suitable acylating agents include acrylic acid, crotonic acid, methacrylic acid, maleic acid, maleic anhydride, fumaric acid, itaconic acid, itaconic anhydride, citraconic acid, citraconic anhydride, mesaconic acid, glutaconic acid, chloromaleic acid, aconitic acid, methylcrotonic acid, sorbic acid, 3-hexenoic acid, 10-decenoic acid, 2-pentene-1,3,5-tricarboxylic acid, cinnamic acid, and lower alkyl (e.g., $C_1$ to $C_4$ alkyl) acid esters of the foregoing, e.g., methyl maleate, ethyl fumarate, methyl fumarate, etc. Particularly preferred are the unsaturated dicarboxylic acids and their derivatives; especially maleic acid, fumaric acid and maleic anhydride.

C. Amines for Use in the Preparation of Bi-Functional and Higher Graftable Monomer Mixtures The amines must be capable of being acylated by the appropriate acylating agent, namely primary or secondary amines. Amines capable of being acylated are disclosed in U.S. Pat. No. 4,320,019, column 4, line 60 to column 6, line 14; U.S. Pat. No. 5,424,367, column 10, line 61 to column 13, line 18; U.S. Pat. No. 5,427,702, column 13, line 5 to column 17, line 32. Each of these disclosures is hereby incorporated by reference herein.

Among the various amine types useful in the practice of this invention are alkylene polyamines, aromatic polyamines, and polyoxyalkylene polyamines.

Some examples of the alkylene polyamines include methyleneamines, ethyleneamines, butyleneamines, propyleneamines, pentyleneamines, hexyleneamines, heptyleneamines, octyleneamines, other polymethyleneamines, the cyclic and higher homologs of these amines such as the piperazines, the amino-alkyl-substituted piperazines, etc. The amines include, for example, ethylene diamine, diethylene triamine, triethylene tetramine, propylene diamine, di(heptamethylene)triamine, tripropylene tetramine, tetraethylene pentamine, trimethylene diamine, pentaethylene hexamine, di(trimethylene)triamine, diaminocyclohexane, diaminopropane, diaminobutane, triaminocyclohexane, as well as other polyaminic materials. Other higher homologs obtained by condensing two or more of the above-mentioned alkyleneamines may be used.

Examples of suitable polyoxyalkylene polyamines are those which have the formulae:

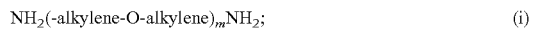

where m has a value of about 3 to 70 and preferably 10 to 35; and

where n has a value of about 1 to 40 with the provision that the sum of all the n's is from about 3 to about 70 and preferably from about 6 to about 35 and R is a polyvalent saturated hydrocarbon radical of up to ten carbon atoms. The alkylene groups in either formula (i) or (ii) may be straight or branched chains containing about 2 to 7, and preferably about 2 to 4 carbon atoms.

The polyoxyalkylene polyamines, such as polyoxyalkylene diamines and polyoxyalkylene triamines, may have average molecular weights ranging from about 200 to about 4000 and preferably from about 400 to about 2000. Suitable polyoxyalkylene polyamines include the polyoxyethylene and polyoxypropylene diamines and the polyoxypropylene triamines having average molecular weights ranging from about 200 to 2000.

Other amine types useful in the practice of this invention include aromatic amines such as benzyl amine and 3-phenyl-1-propyl amine as well as amino-aromatic compounds such as N-arylphenylenediamines represented by the formula:

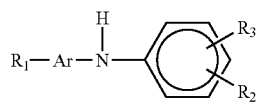

in which Ar is aromatic and $R_1$ is hydrogen, —NH-aryl, —NH-arylalkyl, —NH-alkylaryl, or a branched or straight chain radical having from 4 to 24 carbon atoms and the radical can be an alkyl, alkenyl, alkoxyl, arylalkyl, alkylaryl, hydroxyalkyl or aminoalkyl radical, $R_2$ is —$NH_2$, —(NH($CH_2$)$_n$—)$_m$—$NH_2$, $CH_2$—($CH_2$)$_n$—$NH_2$, -aryl-$NH_2$, in which n and m has a value from 1 to 10, and $R_3$ is hydrogen or an alkyl, alkenyl, alkoxyl, arylalkyl, or alkylaryl radical, which may have from 4 to 24 carbon atoms.

Suitable N-arylphenylenediamine compounds may also be represented by the formula:

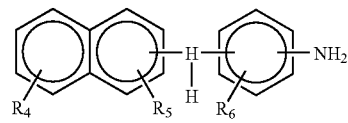

in which $R_4$, $R_5$ and $R_6$ are hydrogen or a linear or branched hydrocarbon radical containing from 1 to 10 carbon atoms and that radical may be an alkyl, alkenyl, alkoxyl, alkylaryl, arylalkyl, hydroxyalkyl, or aminoalkyl radical, and $R_4$, $R_5$ and $R_6$ can be the same or different.

Particularly preferred N-arylphenylenediamines are the N-phenylphenylenediamines, for example, N-phenyl-1,4-phenylenediamine (also referred to herein as 4-aminodiphenylamine), N-phenyl-1,3-phenylenediamine, N-phenyl-1,2-phenylenediamine, N-naphthyl-phenylenediamine, N-phenylnaphthalenediamine and N'-aminopropyl-N-phenylphenylenediamine. Most preferably, the amine is 4-aminodiphenylamine (also called N-phenyl-1,4-phenylenediamine).

Other useful amine types include aminocarbazoles such as those represented by the formula:

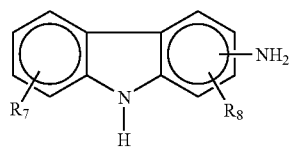

in which $R_7$ and $R_8$ represent hydrogen or an alkyl, alkenyl, or alkoxyl radical having from 1 to 14 carbon atoms, and $R_7$ and $R_8$ can be the same or different;

aminoindoles such as those represented by the formula:

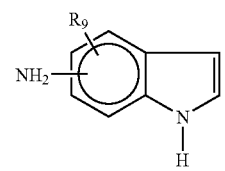

in which $R_9$ represents hydrogen or an alkyl radical having from 1 to 14 carbon atoms, amino-indazolinones such as those represented by the formula:

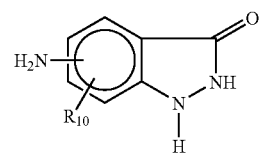

in which $R_{10}$ is hydrogen or an alkyl radical having from 1 to 14 carbon atoms, amino-mercaptotriazole as represented by the formula:

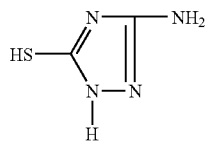

aminoperimidines such as those represented by the formula:

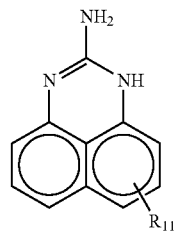

in which $R_{11}$ represents hydrogen or an alkyl or alkoxyl radical having from 1 to 14 carbon atoms.

Other useful amines include: 2-heptyl-3-(2-aminopropyl) imidazoline, 4-methylimidazoline, 1,3-bis-(2-aminoethyl) imidazoline, (2-aminopropyl)-piperazine, 1,4-bis-(2-aminoethyl)piperazine, N,N-dimethyaminopropyl amine, N,N-dioctylethyl amine, N-octyl-N'-methylethylene diamine, and 2-methyl-1-(2-aminobutyl)piperazine, and aminothiazoles from the group consisting of aminothiazole, aminobenzothiazole, aminobenzothiadiazole and aminoalkylthiazole, and aminopyrimidines, such as 2,4,6-triaminopyrimidine.

It is also contemplated that combinations of the above amines may be used to react with one or more acylating agents.

The choice of amine compound will depend, in part, upon the nature of the acylating agent. In the case of the preferred acylating agent, maleic anhydride, those that will react advantageously with the anhydride functionality are most preferred and, therefore, appropriate. Primary amines are preferred because of the stability of the imide products formed. Primary amines, structurally described as $RNH_2$, may be used in which the R group may contain performance enhancing functionalities desirable for the final product. Such properties may include, among others, wear protection, friction reduction and protection against oxidation. Incorporation of elements in addition to carbon, hydrogen and nitrogen, such as, but not limited to, the halogens or sulfur or oxygen, either alone or in combination, is also contemplated.

D. Method for Preparation of Bi-Functional and Higher Graftable Monomer Mixtures A novel method is provided herein of making a bifunctional ethylenically unsaturated, aliphatic or aromatic, nitrogen- and oxygen-containing, graftable monomer, suitable for grafting to a polyalkene to form a dispersant. The method comprises the step of forming an acylating agent mixture comprising a solvent and an acylating agent having at least one point of olefinic unsaturation. The acylating agent may be dissolved or dispersed in the solvent, and the acylating agent mixture may be a solution or dispersion. Suitable solvents include oxygenates such as acetone, base oils, and amides such as N,N-dimethyl formamide. The method also comprises the step of adding a di-amine or higher to the acylating agent mixture, thereby forming a mixture. The di-amine or higher may be added to the acylating agent all at once or slowly, for example, by adding aliquots or metering over a period of time. "Metering" means to add, by drops or continuously, a specific amount over a certain time. The method may comprise the simultaneous metering of the acylating agent and the di-amine into the solvent or premixing the acylating agent and the di-amine prior to mixing the reactants with solvent. The method also comprises the step of heating the mixture. The acylating agent and/or the amine may be heated before, during or after they are combined. The method forms a reaction product of the acylating agent and the amine. The monomer may or may not be recovered from the reaction product before carrying out the grafting reaction. The present methods may also comprise the step of recovering one or more graftable components from the reaction product of the acylating agent and the amine.

The acylating agent and the amine may be provided in suitable molar ratios, though such ratios are not critical for all aspects of the invention. Suitable molar ratios of di-amine to acylating agent include, but are not limited to, the ranges of from about 0.1:1 to about 4:1, from about 0.2:1 to about 4:1, from about 0.5:1 to about 4:1, and from about 1:1 to about 4:1. Where the acylating agents are maleic acid or maleic anhydride, the preferred molar ratios are in the range of from about 0.5:1 to about 3:1.

II. Materials and Methods for Preparation of Dispersant Polyalkenes

A. Polyalkenes for Use in the Preparation Of Dispersant Polyalkenes

A wide variety of polyalkenes (which may or may not have pendant unsaturation) are contemplated for use as a backbone for grafting. Examples of polyalkene contemplated for use include olefin homopolymers, copolymers, and terpolymers, such as, but not limited to, polyethylene, polypropylene, ethylene-propylene polyalkenes, polymers containing two or more monomers, polyisobutene, polymethacrylates, polyalkylstyrenes, partially hydrogenated polyolefins of butadiene and styrene and copolymers of isoprene, such as polymers of styrene and isoprene. EPDM (ethylene/propylene/diene monomer) polymers, such as ethylene-propylene ENB terpolymers, are also contemplated for use.

Materials contemplated for use herein also include ethylene/propylene/diene polyolefins containing from about 15% to about 90% ethylene and from about 10% to about 85% propylene moieties by number, or alternatively, from 30% to about 75% ethylene and from about 25% to about 70% propylene moieties by number. These materials may be optionally modified with from 0% to about 9% diene monomers. Useful diene monomers include 1,4-hexadiene, dicyclopentadiene, 2,5-norbomadiene, 5-ethylidene-2-norbornene, and 1-allyl-4-isopropylidene cyclohexane and combinations of two or more diene monomers.

The low MW polyalkene has a number average molecular weight of from about 300 to about 10,000, preferably from about 500 to about 8,000, or preferably from about 900 to about 5000 or more preferably from about 900 to about 4000. Particularly useful low MW polyalkenes have number average molecular weights from about 1100 to about 3000.

B. Monomers for Use in the Preparation of Dispersant Polyalkenes

The monomers contemplated for use in the preparation of the dispersant polyalkenes include ethylenically unsaturated, aliphatic or aromatic mono-functional monomers described in U.S. patent application Ser. No. 10/444,548 discussed above as well as an ethylenically unsaturated, aliphatic or aromatic bifunctional and higher monomers as described in this disclosure.

C. Initiators for Use in the Preparation of Dispersant Polyalkenes

Broadly, any free-radical initiator capable of operating under the conditions of the reactions as outlined in the present specification is contemplated for use herein. Representative initiators are disclosed in U.S. Pat. No. 4,146,489, column 4, lines 45-53, which is incorporated here by reference. Specific "peroxy" initiators contemplated herein include alkyl, dialkyl, and aryl peroxides, for example: di-t-butyl peroxide (abbreviated herein as "DTBP"), dicumyl peroxide, t-butyl cumyl peroxide, benzoyl peroxide, 2,5-dimethyl-2,5-di(t-butylperoxy)hexane, and 2,5-dimethyl-2,5-di(t-butylperoxy) hexyne-3. Also contemplated are peroxyester and peroxyketal initiators, for example: t-butylperoxy benzoate, t-amylperoxy benzoate, t-butylperoxy acetate, t-butylperoxy benzoate, di-t-butyl diperoxyphthalate, and t-butylperoxy isobutyrate. Also contemplated are hydroperoxides, for example: cumene hydroperoxide, t-butyl hydroperoxide, and hydrogen peroxide. Also contemplated are azo initiators, for example: 2-t-butylazo-2-cyanopropane, 2-t-butylazo-1-cyanocyclohexane, 2,2'-azobis(2,4-dimethylpentane nitrile), 2,2'-azobis(2-methylpropane nitrile), 1,1'-azobis(cyclohexanecarbonitrile), and azoisobutyronitrile (AIBN). Other similar materials are also contemplated such as, but not limited to, diacyl peroxides, ketone peroxides and peroxydicarbonates. It is also contemplated that combinations of more than one initiator, including combinations of different types of initiators, may be employed.

Each such initiator commonly has a characteristic minimum reaction initiation temperature, above which it will readily initiate a reaction and below which the reaction will proceed more slowly or not at all. Consequently, the minimum reaction temperature is commonly dictated by the selected initiator.

D. Methods for Preparation of Dispersant Polyalkene

The grafting reaction may be carried out using one of several reaction methods, namely, (1) radical reaction initiator to promote radical grafting, (2) chlorination procedure or (3) carrying out the "ene" reaction. The grafting reaction may be carried out in solution and a more detailed discussion of this method may be found in U.S. patent application Ser. No. 10/444,548 incorporated above by reference.

When carrying out the radical initiated reaction, both the initiator and the monomer mixture may be used neat. Alternatively, they may be introduced into the polyalkene as a blend with appropriate solvents at a solids concentration ranging from about 15% to about 75%, for example, about 40%. The neat polyalkene fluid is introduced into a suitable well-stirred, heated reactor which can be purged or blanketed with an inerting gas, e.g., nitrogen, carbon dioxide, helium, or argon or otherwise isolated from the ambient air.

The polyalkene is heated to the desired reaction temperature, chosen, in part, so that essentially all of the initiator is consumed during the time allotted for the reaction. For example, if DTBP (di-t-butyl peroxide) is used as the initiator, the reaction temperature should be greater than about 160° C. Since the various acceptable initiators have different optimum reaction temperatures, the choice of a particular initiator may require adjustment of the reaction temperature or, alternatively, adjustment of the reaction time, in order to insure that the reaction conditions are compatible with the choice of initiator.

Consumption of initiator and reaction time are not the only determinants of the reaction temperature chosen, the temperature condition is also used to facilitate mixing and distribution of the reactant as well as maintaining fluidity of the polyalkene. Frequently, temperatures above 160° C. will be employed.

1. Molar Proportion of Monomer

The contemplated proportions of the graftable monomer to the polyalkene and reaction conditions are selected so that an effective percentage (ideally, most or all of the reactant charge) of the graftable monomer will graft onto the polyalkene, rather than forming dimeric, oligomeric, or homopolymeric graft moieties or entirely independent homopolymers. The alternatively contemplated minimum mole ratios of the graftable monomer to the starting polyalkene are as follows:
at least about 0.1 mole,
alternatively at least about 0.2 moles,
alternatively at least about 0.5 moles,
alternatively at least about 0.8 moles,
alternatively at least about 1 mole,
alternatively at least about 2 moles,
alternatively at least about 3 moles,
alternatively at least about 4 moles,
alternatively at least about 5 moles,
alternatively at least about 6 moles,
alternatively at least about 7 moles,
alternatively at least about 8 moles of the graftable monomer per mole of the starting polyalkene.

A contemplated maximum molar proportion of the graftable monomer to the starting polyalkene may be desirable in several situations. For example, it may be preferable to select a contemplated maximum molar proportion of the graftable monomer to the starting polyalkene in order to facilitate manufacturing control of product quality.

The graftable monomer may be introduced into the reactor all at once, in several discrete charges, or at a steady rate over an extended period. The desired minimum rate of addition of the graftable monomer mixture to the reaction mixture is selected from:
at least about 0.1%,
alternatively at least about 0.5%,
alternatively at least about 1.0%,
alternatively at least about 2.0%,
alternatively at least about 5.0%,
alternatively at least about 10%,
alternatively at least about 20%,
alternatively at least about 50%,
alternatively at least about 100% of the necessary charge of graftable monomer mixture per minute. When added over time, the monomer can be added at an essentially constant rate, or at a rate which varies with time. Any of the above values can represent an average rate of addition or the minimum value of a rate which varies with time.

The desired maximum rate of addition is selected from:
at most about 0.5%,
alternatively at most about 1.0%,
alternatively at most about 2.0%,
alternatively at most about 5.0%,
alternatively at most about 20%,
alternatively at most about 100% of the necessary charge of graftable monomer mixture per minute. Any of the above values can represent an average rate of addition or the maximum value of a rate which varies with time.

The graftable monomer may be added as a neat liquid, in solid or molten form, or cut back with a solvent. While it may be introduced neat, it may be cut back with a solvent to avoid high localized concentrations of the monomer as it enters the reactor. In one embodiment, the monomer is diluted with a solvent. The monomer can be diluted by at least about 1 times (50% concentration), alternatively at least about 5 times alternatively at least about 20 times, its weight or volume with a suitable solvent or dispersing medium.

2. Molar Proportion of Initiator

The contemplated proportions of the initiator to the graftable monomer and the reaction conditions are selected so that at least many, and ideally, all of the monomer will graft directly onto the polyolefin, rather than forming dimeric, oligomeric, or homopolymeric graft moieties or entirely independent homopolymers. The contemplated minimum molar proportions of the initiator to the graftable monomer mixture are from about 0.05:1 to about 2:1. No specific maximum proportion of the initiator is contemplated, though too much of the initiator may degrade the polyalkene.

While the initiator may be added neat, in a preferred embodiment, it is introduced "cut-back" with solvent in order to avoid localized regions of elevated concentration. The initiator can be added before, with or after the graftable monomer. For example, the initiator may be added so that, at any given time, the amount of unreacted initiator present is much less than the entire charge, and preferably a small fraction of the entire charge. In one embodiment, the initiator may be added after substantially all the graftable monomer has been added, so there is an excess of both the graftable monomer and the polyolefin during essentially the entire reaction. In another embodiment, the initiator may be added along with the graftable monomer, either at essentially the same rate (measured as a percentage of the entire charge added per minute) or at a somewhat faster or slower rate, so there is an excess of polyolefin to unreacted initiator and unreacted monomer. For this embodiment, the ratio of unreacted initiator to unreacted monomer remains substantially constant during most of the reaction.

The initiator may be introduced into the reactor in several (or, alternatively, many) discrete charges, or at a steady rate over an extended period. The desired minimum rate of addition of the initiator to the reaction mixture ranges from at least about 0.1% of the necessary charge of initiator per minute to alternatively at least about 100% of the necessary charge of initiator per minute. The initiator can be added at an essentially constant rate, or at a rate which varies with time. The above rates can represent an average rate of addition or the minimum value of a rate which varies with time.

The desired maximum rate of addition of the initiator to the reaction mixture may vary from a maximum of at most about 0.1% of the necessary charge of initiator per minute to at about 100% of the necessary charge of initiator per minute. The above rates can represent an average rate of addition or the maximum value of a rate which varies with time.

While the initiator can be added neat, it is preferably cut back with a solvent to avoid high localized concentrations of the initiator as it enters the reactor. In a preferred embodiment, it is substantially diluted with a process fluid. The initiator can be diluted by at least about 5 times, alternatively at least about 10 times, alternatively at least about 20 times, alternatively at least about 50 times its weight or volume with a suitable solvent or dispersing medium.

3. Procedure for Grafting Reaction

After the reactants have been combined, the reaction mixture is preferably mixed with heating for an additional 2 to 120 minutes to complete the reaction. The time required for completion of the reaction can be determined experimentally, for example, by determining when the concentration of nitrogen or of monomer mixture in solution reaches a value at or approaching a minimum pre-established value.

After the reaction has gone essentially to completion, the heat can be removed and the reaction product can be allowed to cool in the reactor with mixing. Alternatively, more aggressive cooling can be employed, using a heat exchanger or other apparatus. Alternatively, the reaction product may be removed while still at or near reaction temperature.

III. Composition and Materials for Preparation of Lubricating Oil Compositions

Composition of Lubricating Oil Compositions

The lubricating oil compositions of the present invention preferably comprise the following ingredients in the stated proportions:

a. from about 70% to about 99% by weight, alternatively from about 80% to about 99% by weight, alternatively from about 88% to about 99% by weight, of one or more base oils;

b. from about 0.0% solids to about 10% solids by weight, alternatively from about 0.05% solids to about 5% solids by weight, alternatively from about 0.15% solids to about 2% solids by weight, alternatively from about 0.15% solids to about 1.5% solids by weight, alternatively from 0.25% solids to about 1.5% solids by weight, alternatively from 0.5% solids by weight to 1.5% solids by weight, of one or more grafted polyolefins dispersant viscosity index improvers;

c. from 0.1% to about 20% by weight, alternatively from about 0.2% to about 15% by weight, alternatively from about 0.5% to about 10% by weight, or alternatively from about 0.5% to about 8%, of one or more dispersants which are grafted polyalkenes made according to the present invention;

d. from 0.0% solids to 10% solids by weight, alternatively from about 0.0% solids to about 5% solids by weight, alternatively from about 0.05% solids to about 2% solids by weight, alternatively from about 0.1% solids to about 1% solids by weight, of one or more non-grafted polyolefins used as viscosity index improvers;

e. from 0.0% to about 10% by weight, alternatively from about 0.2% to about 8% by weight, or alternatively from about 0.5% to about 6%, of one or more dispersants which are not made according to the present invention;

f. from about 0.2% to 6% by weight, alternatively from about 0.3% to 4% by weight, alternatively from about 0.3% to about 3% by weight, alternatively from about 0.3% to about 2% by weight, of one or more detergents;

g. from about 0.01% to 5% by weight, alternatively from about 0.04% to about 4% by weight, alternatively from about 0.06% to about 3% by weight, of one or more anti-wear agents;

h. from about 0.01% to 5% by weight, alternatively from about 0.01% to 3% by weight, alternatively from about 0.05% to about 2% by weight, alternatively from about 0.1% to about 2% by weight, of one or more anti-oxidants; and i. from about 0.0% to 4% by weight, alternatively from about 0.0% to 3% by weight, alternatively from about 0.005% to about 2% by weight, alternatively from about 0.005% to about 1.5% by weight, of minor ingredients such as, but not limited to, friction modifiers, pour point depressants, and anti-foam agents.

The percentages of d through i may be calculated based on the form in which they are commercially available. The function and properties of each ingredient identified above and several examples of ingredients are summarized in the following sections of this specification.

A. Base Oils

Any of the petroleum or synthetic base oils previously identified as process solvents for the graftable polyalkenes of the present invention can be used as the base oil. Indeed, any conventional lubricating oil, or combinations thereof, may also be used.

B. Grafted Polyolefin Dispersant Viscosity Index Improvers

The grafted polyolefins are discussed in more detail in section D below.

C. Dispersant Polyalkenes

The dispersant polyalkene according to the present invention contains:

at least about 0.2 moles,
alternatively at least about 0.5 moles,
alternatively at least about 0.8 moles,
alternatively at least about 1 mole,
alternatively at least about 2 moles,
alternatively at least about 3 moles,
alternatively at least about 4 moles,
alternatively at least about 5 moles,
alternatively at least about 6 moles,
alternatively at least about 7 moles,
alternatively at least about 8 moles, of grafted monomer mixture per mole of the original polyalkene.

D. Grafted and Non-Grafted Polyolefins used as Viscosity Modifiers

The conventional viscosity index improving polyolefins can be used in the formulations according to the present invention. These are conventionally long-chain polyolefins. Several examples of polyolefins contemplated for use herein include polyisobutenes, polymethacrylates, polyalkylstyrenes, partially hydrogenated copolymers of butadiene and styrene, amorphous polyolefins of ethylene and propylene, ethylene-propylene diene polymers, polyisoprene, and styrene-isoprene. Dispersant viscosity modifiers, as taught in U.S. patent application Ser. No. 10/444,548 as well as U.S. Pat. No. 5,523,008 and patents cited therein, can also be used according to the present invention.

E. Conventional Dispersants

Other dispersants also help suspend insoluble engine oil oxidation products, thus preventing sludge flocculation and precipitation or deposition of particulates on metal parts. Suitable dispersants include high molecular weight alkyl succinimides and the reaction products of oil-soluble polyisobutylene succinic anhydride with ethylene amines such as tetraethylene pentamine and borated salts thereof.

Such conventional dispersants are also contemplated for use herein, although frequently they can be used at reduced concentrations when the grafted polyolefins according to the present invention are used. Several examples of dispersants include those listed in U.S. Pat. No. 4,092,255, column 1, lines 3841: succinimides or succinic esters, alkylated with a polyolefin of isobutene or propylene, on the carbon in the alpha position of the succinimide carbonyl. These additives are useful for maintaining the cleanliness of an engine or other machinery.

F. Detergents

Detergents to maintain engine cleanliness can be used in the present lubricating oil compositions. These materials include the metal salts of sulfonic acids, alkyl phenols, sulfurized alkyl phenols, alkyl salicylates, naphthenates, and other soluble mono- and dicarboxylic acids. Basic (vis, overbased) metal salts, such as basic alkaline earth metal sulfonates (especially calcium and magnesium salts) are frequently used as detergents. Such detergents are particularly useful for keeping the insoluble particulate materials in an engine or other machinery in suspension. Other examples of detergents contemplated for use herein include those recited in U.S. Pat. No. 4,092,255, column 1, lines 35-36: sulfonates, phenates, or organic phosphates of polyvalent metals.

G. Anti-Wear Agents

Anti-wear agents, as their name implies, reduce wear of metal parts. Zinc dialkyldithiophosphates and zinc diaryldithiophosphates and organo molybdenum compounds such as molybdenum dialkyldithiocarbamates are representative of conventional anti-wear agents.

H. Anti-Oxidants

Oxidation inhibitors, or anti-oxidants, reduce the tendency of lubricating oils to deteriorate in service. This deterioration can be evidenced by increased oil viscosity and by the products of oxidation such as sludge and varnish-like deposits on the metal surfaces. Such oxidation inhibitors include alkaline earth metal salts of alkylphenolthioesters having preferably $C_5$ to $C_{12}$ alkyl side chains, e.g., calcium nonylphenol sulfide, dioctylphenylamine, phenyl-alpha-naphthylamine, phosphosulfurized or sulfurized hydrocarbons, and organo molybdenum compounds such as molybdenum dialkyldithiocarbamates.

I. Pour Point Depressants and Other Minor Ingredients

Pour point depressants, otherwise known as lube oil flow improvers, lower the temperature at which the fluid will flow or can be poured. Such additives are well known. Typical of those additives which optimize the low temperature fluidity of a lubricant are $C_8$-$C_{18}$-dialkylfumarate vinyl acetate copolymers, and polymethacrylates.

Many minor ingredients which do not prevent the use of the present compositions as lubricating oils are contemplated herein. A non-exhaustive list of other such additives includes rust inhibitors, as well as extreme pressure additives, friction modifiers, antifoam additives, and dyes.

WORKING EXAMPLES

Example 1

Laboratory Preparation of Bi-Functional Monomer for Grafting

In this example, an ethylenically-unsaturated monomer containing both nitrogen and oxygen, having two sites of unsaturation, is prepared. A 500 ml reactor equipped with an electric heating mantle, stirrer, thermometer and water-cooled reflux condenser is charged with about 14 ml of N,N-dimethyl formamide and about 7.0 g of maleic anhydride. The reactor temperature is raised to about 150° C. and allowed to reflux at temperature. While at that temperature, about 5 g of triethylene tetramine are quickly introduced into the solution. The reaction proceeds for about 3 hours and leads to the formation of a mixture of reaction products comprising amic acids and di-maleimide, e.g., the formation of a bi-functional monomer mixture. This reaction mixture, without subsequent purification or separation of components, is suitable for grafting onto a polyalkene.

Example 2

Laboratory Preparation of Graft Low Molecular Weight Polyalkene

A resin kettle equipped with an electric heating mantle, stirrer, thermometer and gas inlet is charged with about 100 g of a neat polyalkene. The gas inlet permits the gas to be fed either below or above the surface of the solution. The polyalkene is heated to 170° C. During heating the polyalkene is purged with an inerting gas ($CO_2$) fed below the surface of the solution. When the polyalkene reaches the appropriate temperature of 170° C., the purge gas is redirected to flow over the surface of the polyalkene. With the polyalkene at temperature, two solutions, one containing the monomer mixture from Example 1 and the other containing di-t-butyl peroxide initiator are introduced. The monomer mixture is prepared by dissolving about 25 g of the monomer from Example 1 in 25 ml of THF. The initiator solution is prepared by dissolving about 10 g of di-t-butyl peroxide in 60 ml of heptane. Five aliquots of the monomer solution are introduced into the resin kettle over a sixty minutes period. The full charge of initiator solution is metered into the resin kettle over the same sixty minutes period. After all of the reactants are added, the mixture is allowed to react for five (5) hours.

Example 3

Laboratory Preparation of Graft Low Molecular Weight Polyalkene

A resin kettle equipped with an electric heating mantle, stirrer, thermometer and gas inlet is charged with about 11.8 g of a neat polyalkene (Indopol H-100) and about 29.8 g of o-dichlorobenzene (about 28% by wt.). The gas inlet permits the gas to be fed either below and/or above the surface of the solution. The mixture of the polyalkene and o-dichlorobenzene is heated to 170° C. During heating the polyalkene solution is purged with an inerting gas ($CO_2$) fed below the surface of the solution. When the polyalkene solution reaches the appropriate temperature of about 170° C., the purge gas is redirected to flow over the surface of the polyalkene solution.

While maintaining the solution at the reaction temperature of 170° C. about 3.43 g of a mono-functional monomer mixture, based upon the reaction between 4-aminophenylenediamine and maleic anhydride, is introduced all at once into the polyalkene solution. A solution containing a total of about 4.2 g of di-t-butyl peroxide initiator in heptane is then delivered over 3 hours. The reactants are refluxed for an additional 45 minutes after all of the t-butyl peroxide solution is introduced. When the reaction is complete, the o-dichlorobenzene is distilled from the reaction mixture at atmospheric pressure. The resultant grafted low molecular weight polyalkene is washed with acetone and is, then, dried under vacuum at 60° C. An IR spectrum of the graft product exhibits peaks at 1600 $cm^{-1}$, 1720 $cm^{-1}$ and 1780 $cm^{-1}$.

Example 4

Laboratory Preparation of Graft Low Molecular Weight Polyalkene

A resin kettle equipped with an electric heating mantle, stirrer, thermometer and gas inlet is charged with about 100 g of a neat polyalkene. The gas inlet permits the gas to be fed either below or above the surface of the solution. The polyalkene is heated to 170° C. During heating, the polyalkene is purged with an inerting gas ($CO_2$) fed below the surface of the solution. When the polyalkene reaches the appropriate temperature of 170° C., the purge gas is redirected to flow over the surface of the polyalkene. With the polyalkene at temperature, two solutions, one containing a mono-functional monomer mixture based upon the reaction between 4-aminophenylenediamine and maleic anhydride and the other containing di-t-butyl peroxide initiator are introduced. The monomer mixture is prepared by dissolving about 22 g of the monomer in 25 ml of THF. The initiator solution is prepared by dissolving about 10 g of di-t-butyl peroxide in 60 ml of heptane. Five aliquots of the monomer solution are introduced into the resin kettle over a sixty minutes period. The full charge of initiator solution is metered into the resin kettle over the same sixty minutes period. After all of the reactants are added, the mixture is allowed to react for five (5) hours.

I claim:

1. A method of making a graft polyalkene dispersant which is a graft reaction product of an ethylenically unsaturated, oxygen- and nitrogen-containing, aliphatic or aromatic reaction product grafted on a polyalkene backbone, the method comprising the steps of (1) reacting an amine and an acylating agent having at least one point of ethylenic unsaturation to form a reaction product, wherein the amine is selected from the group consisting of primary amines and secondary amines, and (2) grafting at least a portion of the reaction product onto a polyalkene backbone having a number average molecular weight of from about 300 to about 10,000 to form a grafted polyalkene, wherein the molar proportion of the grafted portion of the reaction product to the polyalkene backbone is at least about 0.5:1.

2. The method of claim 1, wherein the polyalkene backbone is selected from the group consisting of olefin homopolymers, copolymers and terpolymers.

3. The method of claim 1, wherein the polyalkene backbone is selected from the group consisting of polyethylene, polypropylene, ethylene-propylene copolymers, and ethylene/propylene/diene copolymers.

4. The method of claim 1, wherein the polyalkene backbone is selected from the group consisting of polyisobutene, polymethacrylates, polyalkylstyrenes, partially hydrogenated polyolefins of butadiene and styrene.

5. The method of claim 1 wherein the amine has more than one primary or secondary amine.

* * * * *